(12) United States Patent
Bergmann et al.

(10) Patent No.: US 9,664,600 B2
(45) Date of Patent: May 30, 2017

(54) APPARATUSES AND METHODS FOR FORMING WOUNDS IN CELL LAYERS

(71) Applicants: John S. Bergmann, Galveston, TX (US); Celeste C. Finnerty, League City, TX (US); David N. Herndon, Galveston, TX (US)

(72) Inventors: John S. Bergmann, Galveston, TX (US); Celeste C. Finnerty, League City, TX (US); David N. Herndon, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 184 days.

(21) Appl. No.: 14/337,875

(22) Filed: Jul. 22, 2014

(65) Prior Publication Data

US 2015/0024425 A1    Jan. 22, 2015

Related U.S. Application Data

(60) Provisional application No. 61/856,844, filed on Jul. 22, 2013.

(51) Int. Cl.
*C12M 3/00* (2006.01)
*G01N 1/28* (2006.01)
*C12M 1/42* (2006.01)

(52) U.S. Cl.
CPC ............. *G01N 1/286* (2013.01); *C12M 35/04* (2013.01); *G01N 2001/2873* (2013.01)

(58) Field of Classification Search
CPC .. G01N 1/286; G01N 2001/2873; G01N 3/46; C12M 35/04; B28D 1/225
See application file for complete search history.

(56) References Cited

U.S. PATENT DOCUMENTS

| | | | | |
|---|---|---|---|---|
| 573,843 | A * | 12/1896 | Westenfeld | ........... C03B 33/027 33/32.3 |
| 852,430 | A * | 5/1907 | Goodman | ................ B25H 7/04 33/32.2 |
| 4,553,327 | A * | 11/1985 | Watanabe | ............... B43L 13/02 33/32.2 |
| 2009/0255138 | A1* | 10/2009 | Stoklosa | .................. B25H 7/04 33/32.2 |
| 2011/0179934 | A1* | 7/2011 | Soyama | ............... B28D 5/0023 83/875 |

OTHER PUBLICATIONS

Liang, et al., In vitro scratch assay: a convenient and inexpensive method for analysis of cell migration in vtro; Nature Protoc 2, 329-333, 2007.

(Continued)

*Primary Examiner* — William H Beisner
(74) *Attorney, Agent, or Firm* — Thomas | Horstemeyer, LLP (57) ABSTRACT

In one embodiment, an apparatus for forming wounds in cell layers includes a base that includes a guide track, and a sliding member adapted to fit within the guide track, the sliding member including a scratching element holder adapted to secure a scratching element in a position in which it contacts a cell layer, wherein the sliding member is further adapted to slide along the guide track to drag the scratching element through the cell layer.

21 Claims, 5 Drawing Sheets

(56) References Cited

OTHER PUBLICATIONS

Core, G., Scratch-wound assay; Meth. Mol. biol. 769, 25-30, 2011.
Yarrow, et al., A high-throughout cell migration assay using scratch wound healing, a comparison of image-based readout methods, MBC Biotechnol 4, 21, 2004.
Simpson, et al., Identification of genes that regulate epithellal cell migration using an sIRNA screening approach, Nat. Cell. Biol 9, 1027-1038, 2008.
Gough, et al., A quantitative, facile, and high-throughput Image-based cell migration method is a robust alternative to the scratch assay, J. Biomol. Screen 16, 155-163, 2011.
Turchi, et al., Dynamic characterization of the molecular events during in vitro epidermal wound healing, J. invest. Dermatol, 119, 56-63, 2002.
Lauder, et al., Quantification of the repair process involved in the repair of the cell monolayer using an in vitro model of mechanical injury, Anglogeneisis 2, 67-80, 1998.
Ma, et al., The Cell Comb Scratch Assay for Biochemical Analysis of Cell Wound Repair, EMD Millipore, 2011.

\* cited by examiner

APPARATUSES AND METHODS FOR FORMING WOUNDS IN CELL LAYERS

CROSS-REFERENCE TO RELATED APPLICATION(S)

This application claims priority to co-pending U.S. Provisional Application Ser. No. 61/856,844, filed Jul. 22, 2013, which is hereby incorporated by reference herein in its entirety.

NOTICE OF GOVERNMENT-SPONSORED RESEARCH

This invention was made with Government support under grant or contract number P50-GM060338, awarded by the National Institute of General Medical Sciences (NIGMS). The Government has certain rights in the invention.

BACKGROUND

Cell migration is fundamental to a variety of biological processes, including embryonic development, angiogenesis, wound healing, immune response, and inflammation. While cell migration can be studied using a variety of methods, the scratch assay is most commonly used because of the simplicity of the required materials, experimental setup, data collection, and interpretation. The scratch assay is typically performed by scratching a confluent cell monolayer with a pipette tip to create a narrow gap or "wound." Shortly after wounding, the cells along the edge of the wound begin to migrate into the gap. This process continues until the gap has been completely repopulated with cells. The extent of wound closure is typically quantified by light microscopy, and molecular events occurring during the wound healing process can be characterized by immunofluorescence. Advances in understanding the repair mechanisms of wounded cell monolayers have been facilitated by the development of methods for performing the assay in multi-well plates. Such methods include delivering wounds to existing monolayers in the wells or occlusion of the center of the well during monolayer formation to create a gap. Each method then involves quantification of the extent of cell migration into the gap.

In most cases, wounds are formed in the cell monolayers by hand. Specifically, a pipette tip is held in the hand and is manually dragged along the monolayer to form the wound. Although this method is effective in forming wounds, the wounds that result can be of non-uniform width because of the difficulty associated with steadily drawing the pipette tip across the cell monolayer. The non-uniformity that results is undesirable because the interpretation of the results of the scratch assay may depend at least in part upon a presumed specific width of the wound. In addition, if more than one wound is required, uniformity of wound spacing is difficult to achieve. In view of this, it can be appreciated that it would be desirable to have an apparatus and method for forming wounds in cell layers that provide greater wound uniformity.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have an apparatus and method for forming wounds in cell layers that provide greater wound uniformity. Disclosed herein are examples of such apparatuses and methods. In one embodiment, an apparatus comprises a base that supports a sliding member above a working surface, such as a table top. A scratching element holder is mounted to the sliding member that is adapted to support a scratching element, such as a pipette tip, within a desired distance from the working surface. When a layer of cells is placed beneath the sliding member, the scratch element holder can be adjusted to place a tip of the scratch element in contact with the surface upon which the cell layer is formed with a desired angle and force. The scratch element tip can then be dragged across the surface by sliding the sliding member along the base to form one or more uniform, linear wounds.

In the following disclosure, various specific embodiments are described. It is to be understood that those embodiments are example implementations of the disclosed inventions and that alternative embodiments are possible. All such embodiments are intended to fall within the scope of this disclosure.

Figure 1:
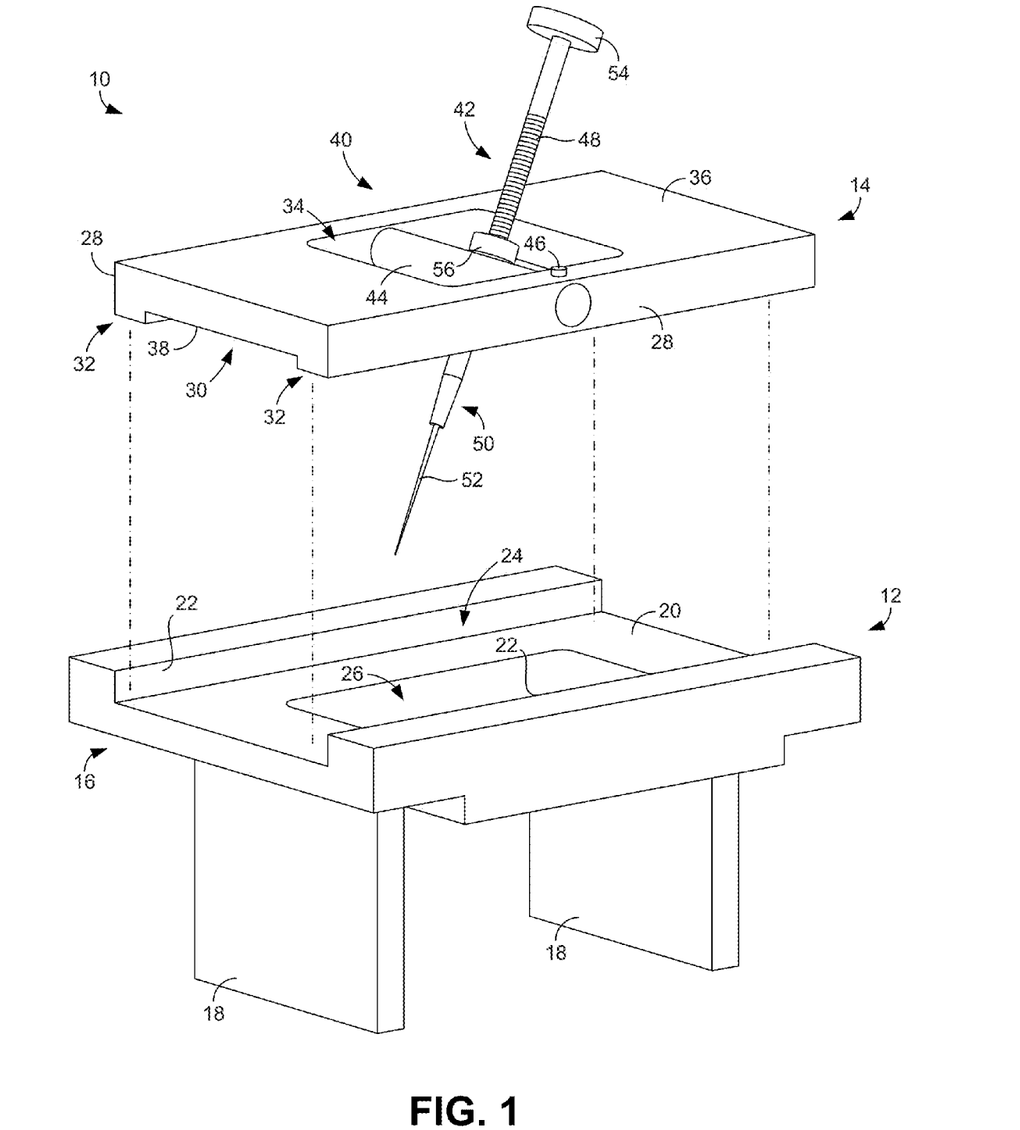
FIG. 1 is an exploded perspective view of a first embodiment of an apparatus for forming wounds in cell layers.

FIG. 1 illustrates an exploded perspective view of a first embodiment of an apparatus 10 for forming wounds in cell layers, such as a confluent cell monolayer. As shown in the figure, the apparatus 10 generally includes a base 12 and a sliding member 14 that is adapted to be received and supported by the base. The base 12 and sliding member 14 can be made of any suitable material, such as a metal or polymeric material. In the illustrated embodiment, the base 12 includes a generally horizontal platform 16 that is supported above a working surface, such as a flat, horizontal table top, with generally vertical legs 18. In some embodiments, the legs 18 support the platform 16 in a manner in which the bottom of the platform is positioned approximately 6 to 10 cm above the working surface.

The platform 16 of the base 12 forms an elongated, planar sliding surface 20 that is adapted to directly support the sliding member 14 and to enable it to slide along a longitudinal axis of the platform and sliding surface. In the illustrated embodiment, the sliding surface 20 is configured as a generally rectangular depression whose lateral edges are defined and bordered by opposing lateral walls 22. As is described below, the sliding surface 20 and the lateral walls 22 together define a linear guide track 24 that enables sliding of the sliding member 14 along the longitudinal axis of the sliding surface but that limits lateral movement of the sliding member so as to ensure the formation of linear wounds. In some embodiments, the sliding surface 20 is approximately 10 to 15 cm long and approximately 5 to 10 wide.

As is also shown in FIG. 1, an opening 26 is formed through the sliding surface 20. This opening 26 extends through the platform 16 to its bottom surface so that the working surface can be accessed from the guide track 24. In the illustrated embodiment, the opening 26 is an elongated opening whose longitudinal axis is aligned with the longitudinal axes of the platform 16 and sliding surface 20.

The sliding member 14 is adapted to be received within the guide track 24. In some embodiments, the sliding member 14 is a generally rectangular member that has length and width dimensions similar to the length and width dimensions of the sliding surface 20. In such a case, the sliding member 14 fits within the guide track 24 with its lateral edges 28 in close proximity to or in contact with the lateral walls 22 of the guide track (see FIG. 2). As is shown in FIG. 1, the bottom of the sliding member 14 can include a groove 30 that defines lateral rails 32 upon which the sliding member can slide. In such a case, friction between the sliding member 14 and the sliding surface 20 is reduced so as to enable easier sliding.

An opening 34 is formed through the sliding member 14 that extends from its top surface 36 to its bottom surface 38. In the illustrated embodiment, the opening 34 is generally rectangular. Irrespective of the shape of the opening 34, the sliding member 14 includes a mounting apparatus 40 that is adapted to support a scratching element holder 42. In the illustrated embodiment, the mounting apparatus 40 includes a pivot shaft 44 that is pivotally mounted within the opening 34. More particularly, the pivot shaft 44 extends across the width of the opening 34 so that its longitudinal (pivot) axis is generally perpendicular to the longitudinal axis of the sliding member 14. As described below, the pivot shaft 44 can pivot or rotate within the opening 34 to adjust the orientation of the scratching element holder 42 and, therefore, the position of the tip of the scratching element (described below). The angular position of the pivot shaft 44 can be fixed with a locking element 46. In some embodiments, the locking element 46 comprises a set screw that threads through an opening formed in the top surface 36 of the sliding member 14 that leads to the outer surface of the pivot shaft 44.

As mentioned above, the mounting apparatus 40 supports the scratching element holder 42. In the illustrated embodiment, the holder 42 is an elongated element that extends through an opening (not visible in FIG. 1) formed through the pivot shaft 44 at a medial position along its length. In such cases, the scratching element holder 42 extends both above and below the sliding member 14. Provided at a distal or bottom end of the holder 42 is a scratching element support 50 that is adapted to releasably secure a disposable scratching element 52, such as a pipette tip. In some embodiments, the scratching element support 50 employs a friction fit to secure the scratching element 52. In some embodiments, the support 50 includes an opening that has a diameter that is similar to the outer diameter of the scratching element 52 into which the element can be inserted. In some embodiments, the scratching element 52 can be a 20, 200, or 1000 µl pipette tip and the distal end of the pipette tip can be on the order of 1 mm in diameter.

In some embodiments, the opening formed in the pivot shaft 44 is a threaded opening and the scratching element holder 42 includes a threaded shaft 48 that threads into the opening. In such a case, the scratching element support 50 can be mounted to the distal or bottom end of the holder shaft 48 and the linear position of the support and the scratching element 52 it secures can be adjusted by threading the holder shaft into or out of the pivot shaft 44. This threading can be facilitated by an adjustment knob 54 mounted to the proximal or top end of the threaded shaft 48. In such cases, the scratching element holder 42 can further include a locking element 56 that can be used to fix the linear position of the holder shaft 48 relative to the pivot shaft 44. In some embodiments, the locking element 56 comprises one or more threaded nuts.

Figure 2:
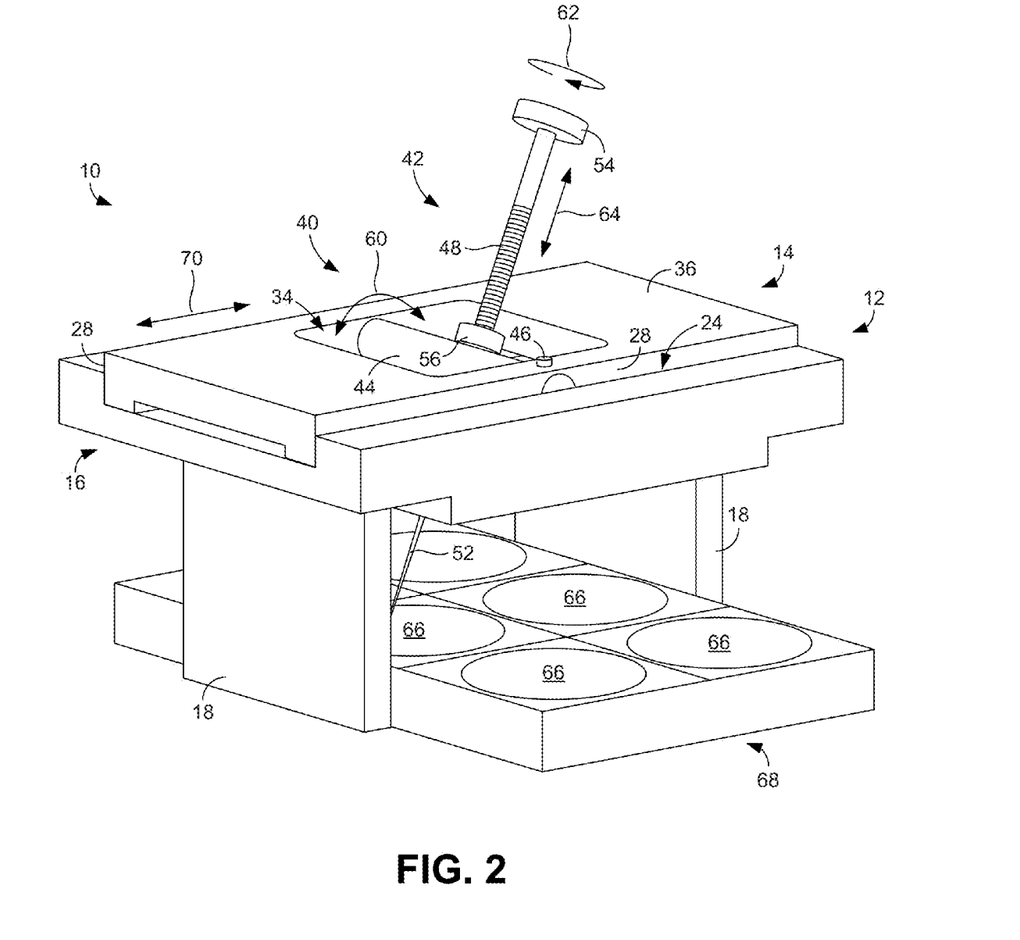
FIG. 2 is a perspective view of the apparatus of FIG. 1 after assembly and illustrates use of the apparatus with a well plate.

With the above-described configuration of the sliding member 14, the tip of the scratching element 52 can be placed in nearly any desired position beneath the platform 16. Such placement is made possible through adjustment of the angular position of the pivot shaft 44 and the linear position of the holder shaft 48. Such adjustment is illustrated in FIG. 2, which shows the apparatus 10 after being assembled by placing the sliding member 14 into the guide track 24 of the base 12 with the scratching element holder 42 extending through the opening 26 of the base platform 16. As shown in this figure, the pivot shaft 44 can be rotated in the directions identified by arrow 60 to adjust the angle that the scratching element 52 forms with the working surface, and the adjustment knob 54 can be rotated in the directions identified by arrow 62 to linearly displace the threaded shaft 48 along the directions identified by arrow 64 (the scratching element 52 being linearly displaced in similar manner). With such functionality, the tip of the scratching element 52 can be placed in contact with the base of one of the wells or dishes 66 of a well plate 68 that has been positioned below the platform 16 and between the legs 18 of the base 12. As is further illustrated in FIG. 2, the sliding member 14 can be slid along the guide track 24 formed by the base 12 in the directions identified by arrow 70. With this functionality, a uniform, linear wound can be easily formed through a cell layer formed on the base of the dish 66.

Figure 3A:
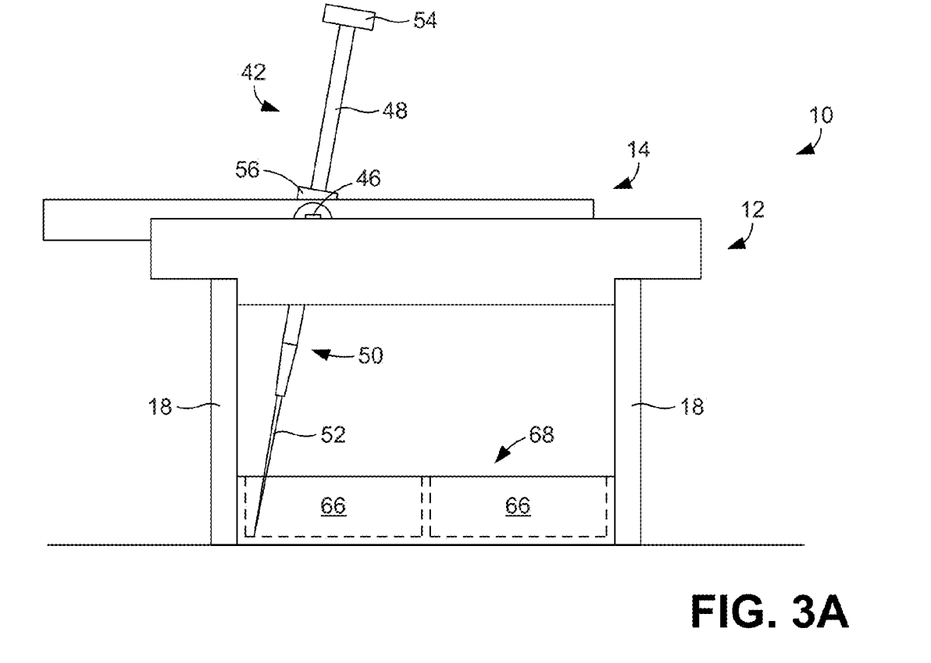
FIGS. 3A-3C are side views of the apparatus of FIG. 1 illustrating an example of use of the apparatus.

FIGS. 3A-3C illustrate an example of forming wounds in wells of a well plate 68. Beginning with FIG. 3A, the sliding member 14 has been positioned to the left (in the orientation of the figure) so that a wound can be formed in a first well 66 of the well plate 68. In addition, the scratching element holder 42 has been adjusted so that the tip of the scratching element 52 is placed into firm contact with the base of the well 66 near the left wall of the well. Once the scratching element 52 has been placed in this position, the pivot shaft 44 and the holder shaft 48 can be locked using the locking elements 46 and 56, respectively.

Figure 3B:
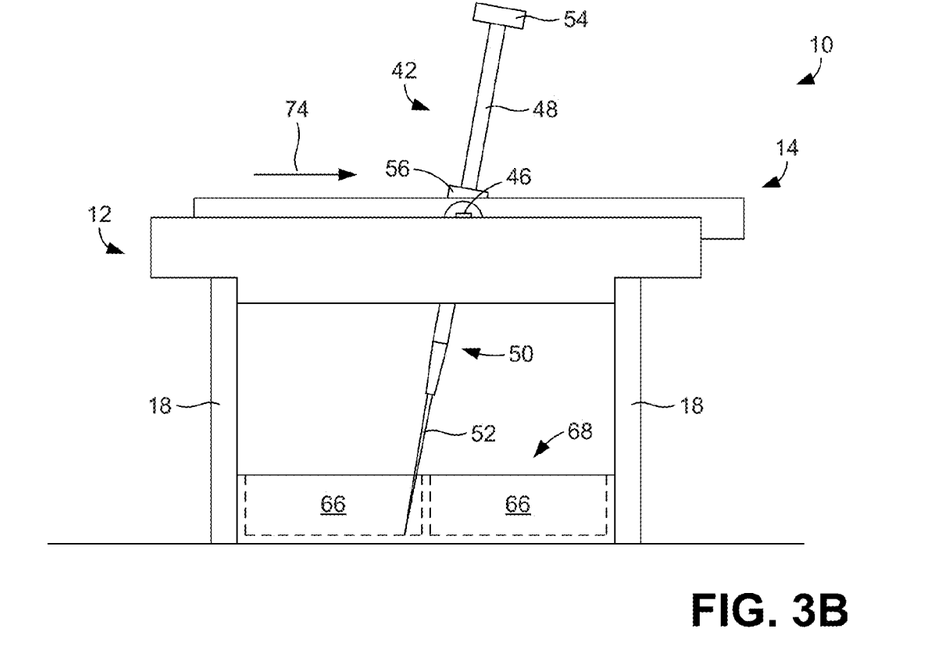

Referring next to FIG. 3B, the sliding member 14 can then be slid to the right (in the orientation of the figure) so as to drag the tip of the scratching element 52 in the direction of arrow 74 along the base of the well 66 from its left wall to its right wall. This results in a uniform, linear wound being formed in the cell layer at the base of the well 66. Other wounds can be formed in the cell layer of the well 66 by lifting the sliding member 14 out of the guide track 24, shifting the lateral position of the well plate 68 by a few millimeters or centimeters (into or out of the page), and setting the sliding member back in the guide track in the position identified in FIG. 3A. If the sliding member 14 is again slid to the right in the manner depicted in FIG. 3B, a second linear wound will be formed that is parallel to the previous wound. Accordingly, multiple parallel, linear wounds of uniform width can be formed in the cell layer, if desired.

Figure 3C:
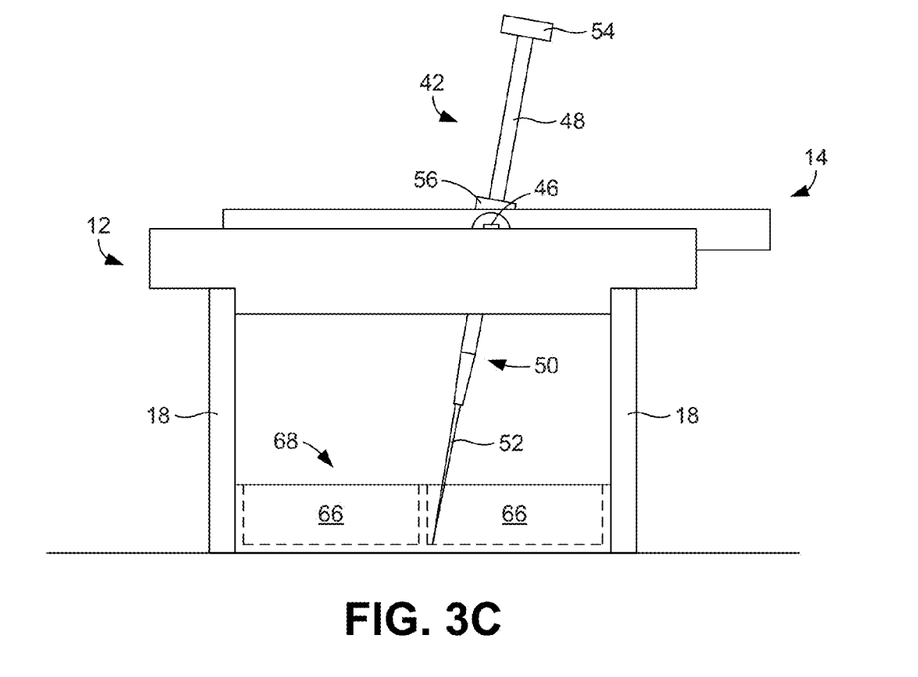

With reference next to FIG. 3C, similar wounds can be formed in the next well 66 of the well plate 68 by lifting the sliding member 14 out of the guide track 24 and repositioning the member along the track.

Although removal of the sliding member 14 from the guide track 24 has been described above, it is noted that, in other embodiments, the scratching element holder 42 can be retracted so that the tip of the scratching element 52 can be lifted up from the well plate 68 without removal of the sliding member from the guide track. For example, in alternative embodiments, the scratching element holder 42 can be spring biased toward the orientations shown in FIGS. 3A-3C but can be pulled away from the sliding member 14 against the force of the spring to lift the scratching element 52. Once an adjustment is made to either the sliding member 14 or the well plate 68, the scratching element holder 42 can be permitted to return to its original position under the force of the spring.

Figure 4:
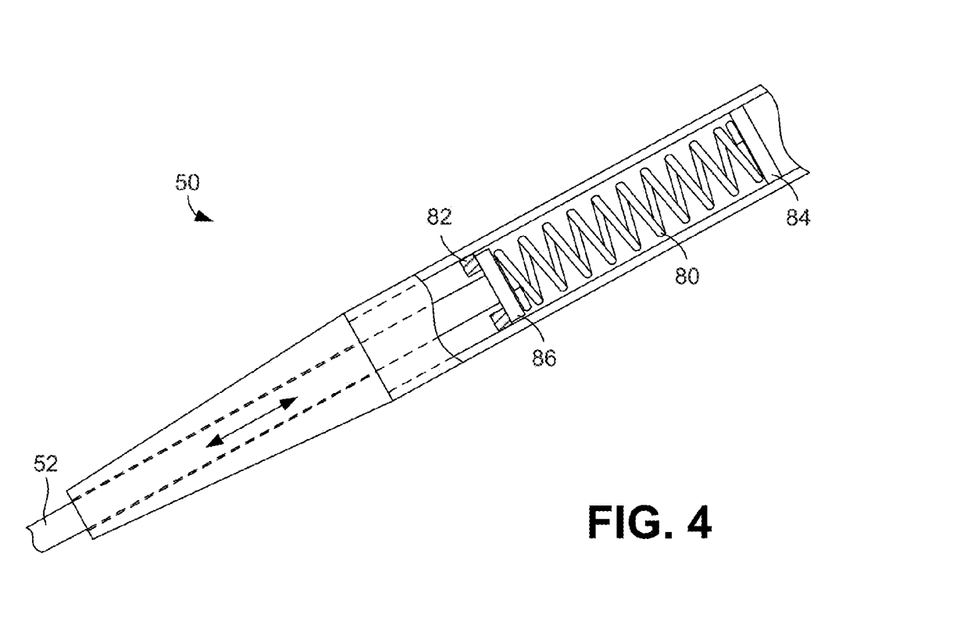
FIG. 4 is a detail view of a scratching element support shown in FIGS. 1 and 2, illustrating an embodiment of a biasing mechanism of the support.

FIG. 4 illustrates an example biasing mechanism that can be used to bias the scratching element 52. In the example of FIG. 4, the biasing mechanism includes a coiled spring 80 that is contained in the scratching element support 50. The spring 80 is held in compression between two end stops 82 and 84 positioned at opposite ends of the spring that limit the spring's expansion. The mechanism further includes an element 86 that prevents the scratching element 52 from passing through the spring 80. During use of the apparatus 10, the spring 80 applies downward pressure to the scratching element 52 to bias the scratching element toward an extended position. If upward linear pressure is applied to the scratching element 52, the element will compress the spring 80 and move (retract) further into the scratching element support 50. Accordingly, the biasing mechanism ensures that the scratching element 52 contacts the cell layer without applying too great a force to the layer.

Experiments were performed using a prototype apparatus having a configuration similar to that illustrated in FIGS. 1 and 2. Normal neonatal human dermal fibroblasts (PCS-201-010, American Type Culture Collection Rockville, Md.) and two primary cell lines (#79 hypertrophic scar (HTS) and #80 non-burn skin (NBS)) isolated from a burn patient were cultured in complete DMEM (cDMEM) consisting of 15% (v/v) fetal bovine serum and 1% (v/v) antibiotic antimycotic solution (Cellgro, Corning). All cell lines were maintained in cDMEM at 37° C. and 5% $CO_2$ using standard tissue culture protocols. Corning 12-well culture dishes were scribed on the outside bottom center of the plate with a horizontal line before coating them with 50 µg/ml rat tail collagen. The dishes were then seeded with 2 ml of $4\times10^4$ cells/ml in DMEMc. The cells were cultured for 24 hours, at which time the media was changed to DMEM consisting of 2% (v/v) fetal bovine serum and 1% (v/v) antibiotic antimycotic solution prior to performing the scratch-wound assay 24 hours later.

Two scratch wounds were formed per well using the prototype apparatus. Before the pipette tip was mounted, the scratching element holder angle was adjusted to 80° from horizontal and locked. A sterile pipette tip was then inserted into the holder and adjusted up or down for optimal contact with the plate surface. A horizontal motion was used to slide the holder across the base and denude a strip of cells. Scratch wounds were made by lifting the holder, aligning the plate, placing the holder in the guide track, and sliding the holder. This process was repeated to produce a second scratch wound. The scratch wounds were made perpendicular to the scribed line. This allowed for the rapid and precise location of four observation areas (two above and two below the scribed line), which were monitored at time zero (just after inducing the scratch wounds) and eight hours after wounding. After scratch-wounding, the cells were rinsed twice with 1 ml of 2% DMEM before 2 ml of 2% DMEM was added back to wells. Photomicrographs were immediately taken (i.e., time 0) using a 4× objective mounted on a Nikon 300 Diaphot microscope equipped with a Cool Snap ES2 digital camera. At eight hours after wounding, the previously photographed time 0 areas were re-photographed.

Figure 5:
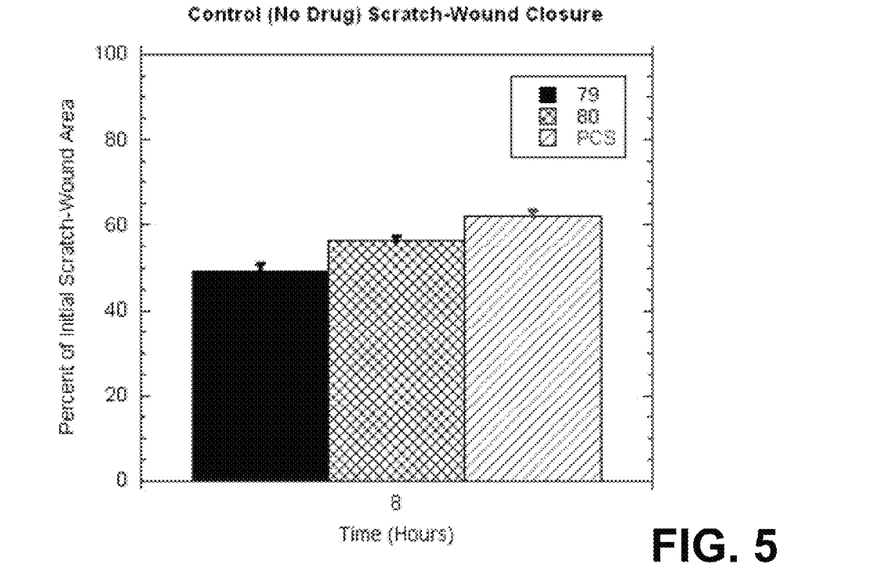
FIG. 5 is a graph that provides a comparison of scratch wounds formed using a prototype apparatus for forming wounds in cell layers.

Images of scratch wound areas at time zero and eight hours were analyzed with TScratch software that enables objective and reproducible quantification of the scratch wound areas. Data are reported as the mean SEM and are shown in FIG. 5. Statistical analysis was performed using one-way ANOVA and reported as significant at $p<0.05$.

Figure 6:
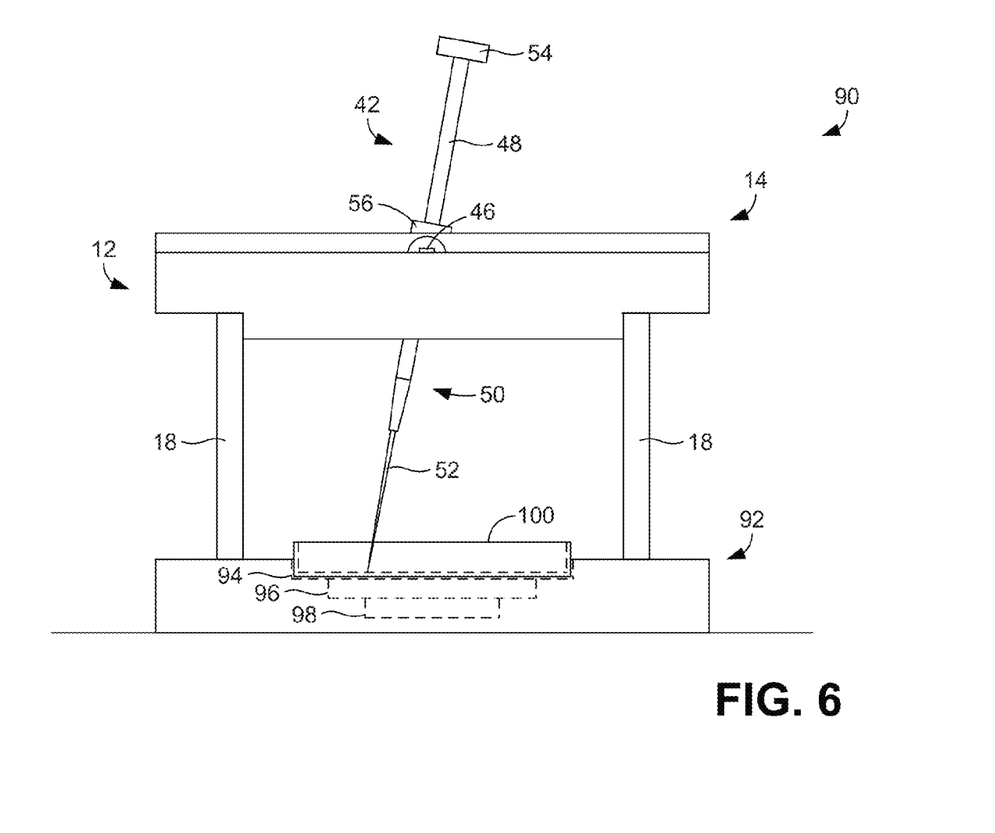
FIG. 6 is a side view of a second embodiment of an apparatus for forming wounds in cell layers plated in various sizes of tissue culture dishes.

FIG. 6 illustrates a second embodiment of an apparatus 80 for forming wounds in cell layers. The apparatus 90 is similar in many ways to the apparatus 10 shown in FIGS. 1-3 and therefore shares many of the same components. The apparatus of FIG. 6, however, is specifically configured to receive and support individual culture dishes. As shown in FIG. 6, the legs 18 of the base 12 are supported by a bottom platform 92. Formed in a central portion of the bottom platform 92 are concentric circular depressions 94-98 that are adapted to receive circular culture dishes of standard sizes, such as 100, 60, and 35 mm. With this configuration, culture dishes, such as the dish 100 shown in FIG. 6, can be securely held relative to the base 12 to facilitate wound formation.

As noted above, various modifications can be made to the disclosed apparatuses. For example, although the scratching element can comprise a disposable pipette tip, in other embodiments it can comprise a disposable or reusable element having a low-friction tip, such as a polytetrafluoroethylene (PTFE) ball tip, which more easily slides across the base of the dish on which the cell layer is formed. Alternatively, the scratching element can comprise a PTFE pipette tip. Notably, PTFE is less compressible than many other polymers. Therefore, a PTFE scratching element will flex less, which further increases scratch uniformity.

In still other embodiments, the scratching element can comprise multiple, equally-spaced tips so as to have a rake-like configuration. In such cases, multiple parallel wounds can be simultaneously formed. In yet other embodiments, the scratching element can be replaced with a cutting element, such as a scalpel, to enable the formation of uniform, linear incisions in a layer or an object. All such variations are considered to be within the scope of the present disclosure.

The invention claimed is:

1. An apparatus for forming wounds in cell layers, the apparatus comprising:
   a base that includes a guide track; and
   a sliding member adapted to fit within the guide track, the sliding member including a scratching element holder adapted to secure a scratching element in a position in which it contacts a cell layer, wherein the sliding member is further adapted to slide along the guide track to drag the scratching element through the cell layer, wherein the scratching element holder mounts to the sliding member with a mounting apparatus.

2. The apparatus of claim 1, wherein the base comprises a platform in which the guide track is formed and one or more legs that support the platform over a working surface.

3. The apparatus of claim 2, wherein the base further comprises an opening that extends through the platform from the guide track to a bottom of the platform.

4. The apparatus of claim 1, wherein the guide track comprises a planar sliding surface and lateral walls that define lateral edges of the sliding surface.

5. The apparatus of claim 1, wherein the sliding member includes lateral rails that support the member within the guide track.

6. The apparatus of claim 1, wherein the mounting apparatus comprises a pivot shaft to which the scratching element holder is mounted that is adapted to adjust an angle of the holder and the scratching element it secures.

7. The apparatus of claim 6, wherein the sliding member includes an opening that extends from a top surface to a bottom surface of the member, and wherein the pivot shaft is mounted within the opening.

8. The apparatus of claim 6, wherein the scratching element holder comprises a threaded shaft that is threaded into a threaded opening of the pivot shaft, wherein a linear position of the scratching element holder and the scratching element it secures can be adjusted by threading the holder shaft into or out of the pivot shaft.

9. The apparatus of claim 8, wherein the mounting apparatus further comprises locking elements that can be used to lock the angular and linear positions of the scratching element holder.

10. The apparatus of claim 9, wherein the locking elements include a set screw that locks the angular position of the pivot shaft and a threaded nut that locks the linear position of the holder shaft.

11. The apparatus of claim 1, wherein the scratching element holder comprises a scratching element support that is adapted to releasably secure the scratching element.

12. The apparatus of claim 11, wherein the scratching element support comprises a biasing mechanism that biases the scratching element toward an extended position.

13. The apparatus of claim 12, wherein the biasing mechanism includes a spring provided within the scratching element support.

14. The apparatus of claim 1, wherein the base further includes a base platform having one or more depressions adapted to receive a culture dish.

15. The apparatus of claim 14, wherein the base platform comprises multiple concentric depressions, each adapted to receive a culture dish of a different size.

16. An apparatus for forming wounds in cell layers, the apparatus comprising:
a base that includes a platform that is supported above a work surface by spaced legs, the platform defining a guide track having a planar sliding surface and lateral walls that define lateral edges of the sliding surface, wherein the platform includes a first opening that extends through the platform from the sliding surface to a bottom of the platform; and
a sliding member adapted to fit within the guide track of the platform, the sliding member including a second opening that passes through a top surface of the member to a bottom surface of the member, the sliding member further including a scratching element holder adapted to secure a scratching element in a position in which it contacts a cell layer, the scratching element holder being mounted to the sliding member with a pivot shaft that is positioned within the second opening, the pivot shaft being adapted to adjust an angle of the holder and the scratching element it secures, the scratching element holder including a threaded shaft that is threaded into a threaded opening of the pivot shaft, wherein a linear position of the scratching element holder and the scratching element it secures can be adjusted by threading the holder shaft into or out of the pivot shaft;
wherein the sliding member is adapted to slide along the guide track to drag the scratching element through the cell layer.

17. The apparatus of claim 16, wherein the sliding member includes lateral rails that support the member within the guide track.

18. The apparatus of claim 16, further comprising locking elements that can be used to lock the angular and linear positions of the scratching element holder.

19. The apparatus of claim 18, wherein the locking elements include a set screw that locks the angular position of the pivot shaft and a threaded nut that locks the linear position of the holder shaft.

20. The apparatus of claim 16, wherein the scratching element holder comprises a scratching element support that is adapted to releasably secure the scratching element.

21. The apparatus of claim 20, wherein the scratching element support includes a biasing mechanism that biases the scratching element toward an extended position.

* * * * *